United States Patent [19]

Ririe

[11] 4,101,282
[45] Jul. 18, 1978

[54] SAMPLE CONDITIONER AND ANALYZER

[75] Inventor: Otis E. Ririe, Bartlesville, Okla.

[73] Assignee: Phillips Petroleum Company, Bartlesville, Okla.

[21] Appl. No.: 770,252

[22] Filed: Feb. 18, 1977

[51] Int. Cl.² .................... G01N 1/22; G01N 31/00
[52] U.S. Cl. .................... 23/254 R; 73/1 G; 73/23; 73/421.5 R
[58] Field of Search ............ 23/232 R, 254 R, 255 R, 23/259, 253 PC, 232 E, 254 E, 255 E; 73/23, 23.1, 421.5 R

[56] References Cited

U.S. PATENT DOCUMENTS

| 3,897,211 | 7/1975 | Ririe, Jr. .................... 23/254 R |
| 3,960,500 | 6/1976 | Ross et al. .................... 23/254 E |

Primary Examiner—Joseph Scovronek

[57] ABSTRACT

A sample containing reactive component is preconditioned in a sample conditioner in a manner which precludes reactions therein and passed to an analyzer through a conduit located in a passageway maintained at a desired temperature by heat exchange with hot air. After the analysis is completed, the sample is purged from the analyzer through the separate conduit extending from the analyzer through said passageway back to the sample conditioner.

6 Claims, 6 Drawing Figures

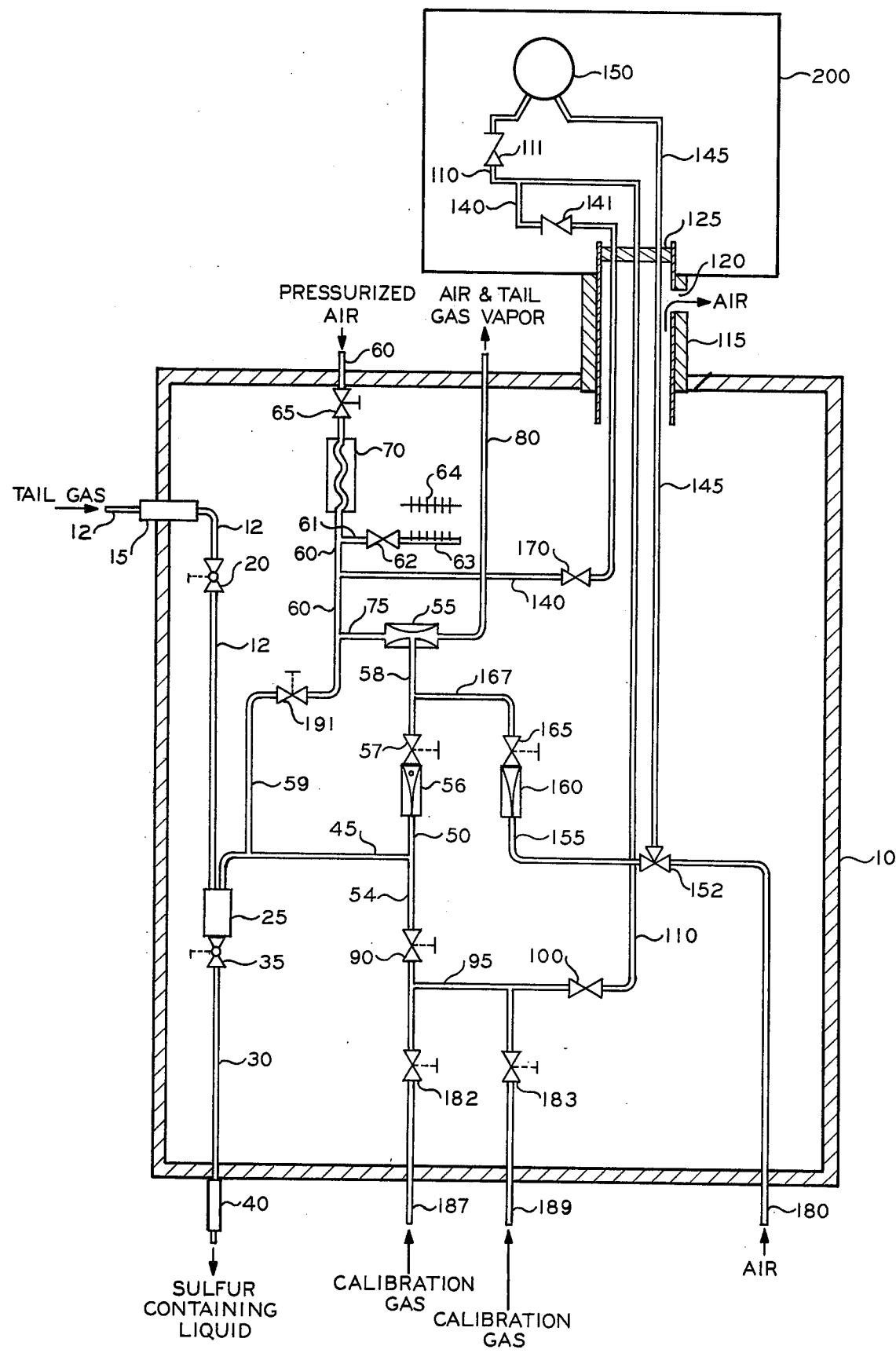

SAMPLE CONDITIONER AND ANALYZER

BACKGROUND OF THE INVENTION

This invention relates to a system for analysis of a gaseous sample containing one or more gases therein. In particular, it relates to a system having an analyzer and a conditioner in which the sample can be prepared for analysis without reactions which affect the results of the analyses.

This invention is especially useful in determining the level of hydrogen sulfide in a gaseous stream. The recovery of sulfur from gaseous streams containing hydrogen sulfide is a fairly common operation in gas and petroleum industries. Such recovery results in both production of elemental sulfur and a reduction of atmospheric pollution. Sulfur is commonly produced by processes such as the Claus process, which involves the reaction of hydrogen sulfide and sulfur dioxide. The optimum reaction conditions of a typical sulfur recovery unit include a specific ratio of sulfur dioxide to hydrogen sulfide in the reactor. Since the same ratio is believed to exist throughout the system, the ratio in the reactor can be determined by the analysis of residual or tail gases from the operation. Sampling of the tail gases is complicated by the presence of elemental sulfur and sulfur compounds therein, and by the reaction between hydrogen sulfide and sulfur dioxide if liquid water is present. Furthermore, sulfur vapors and sulfur aerosols in the sample can condense and deposit along the interior of the sample handling equipment causing additional analysis problems.

To solve these problems, a system for conditioning gaseous samples was provided. Such a system is described in U.S. Pat. No. 3,897,211, the disclosure of which is incorporated herein by reference.

The present invention represents a further improvement of the process and apparatus for the analysis of gaseous samples containing reactive gases such as hydrogen sulfide and sulfur dioxide.

Thus, one object of the present invention is to provide an improved system and method for the analysis of gaseous streams.

Another object of the invention is to provide a system and a method for the analysis of the ratio of hydrogen sulfide and sulfur dioxide, in which system the reaction between these two reactive materials is prevented throughout the sampling and analysis.

A still further object of the invention is to provide a system and a method for analysis of the ratio of hydrogen sulfide to sulfur dioxide, which system has an improved reliability and requires minimum maintenance.

Still another object of the invention is to provide a method and apparatus for determining the amount of hydrogen sulfide and sulfur dioxide in a gaseous stream with an improved accuracy.

Other objects of the invention will become apparent to those skilled in the art upon studying this disclosure.

SUMMARY OF THE INVENTION

A sample containing reactive components is preconditioned in a sample conditioner in the manner which precludes reactions of the reactive components therein, and then passed to a sample analyzer through a conduit which is maintained by means of hot air circulating around it. The sample is analyzed and then purged through the separate backflush line extending from the analyzer through said heat passageway back to the conditioner.

BRIEF DESCRIPTION OF THE DRAWING

The FIGURE depicts the preferred embodiment of the system of the present invention including the preconditioner and the analyzer.

DETAILED DESCRIPTION OF THE INVENTION

The invention will be better understood by describing the specific embodiment thereof illustrated in the FIGURE. The system shown is desired for the analysis of gaseous sample from tail gas which contains water vapors, vaporized sulfur, hydrogen sulfide, and sulfur dioxide.

Referring now to the FIGURE, the gaseous sample obtained by a conventional sample withdrawal probe (not shown) enters conditioning chamber or cabinet 10 through a horizontal sample line 12 and is heated therein by steam in a steam jacket 15 which surrounds the entrance portion of the sample line 12. The temperature of the sample, as it leaves the jacket section of the line 12, is in the range from about 300° F to about 400° F (149° – 20420 C). The cabinet 10 is a metal cabinet, preferably made of steel having heat insulating material on its inner surface. The air inside the cabinet is heated to a temperature in the range from about 300° F to about 400° F (149° – 204° C) by conventional finned tube heaters shown schematically at 64 located within the cabinet. The sample gas passes through a normally open block valve 20 into a liquid-vapor separator 25 which can be of any suitable type, such as the flow reversal or centrifugal type.

In the liquid-vapor separator 25, the sample is subdivided into vapor and liquid phases. The liquid phase, which contains principally sulfur, is periodically removed from the bottom of the liquid-vapor separator 25 via exit line 30 by opening a normally closed block valve 35. Outside the cabinet, line 30 is enveloped by a steam jacket 40 which maintains the temperature of the exit line 30 at a sufficiently high level to keep the sulfur in the liquid state. Liquid-vapor separator 25 consists of a short section of one-inch pipe with pipe reducers on each end to afford connections to sample line 12 and valve 35. It is sold as part no. S03770 by Applied Automation, Inc., Pawhuska Road, Bartlesville, Okla., 74004.

The vapor from the liquid-vapor separator 25, passed through line 45, is subdivided to flow into lines 50 and 54. The majority of vapors is caused to flow through the bypass line 50 as the result of sub-atmospheric pressure created therein. The sub-atmospheric pressure in line 50 is caused by the flow of air through aspirator 55, which is preferably a venturi-type vacuum source, such as a vacuum transducer purchased from Air-Vac Engineering Co., Inc., Milford, Connecticut. The air that flows through the aspirator 55 enters under pressure through line 60. The flow in line 60 is controlled by flow control valve 65. The air passes through flow control valve 65 and enters a heater 70 where the air is heated to a temperature of about 300° F (149° C). The heated air is passed by line 75 through venturi aspirator 55, which passage results in the creation of the previously referred to sub-atmospheric pressure in line 50. Heated air from line 60 also flows through line 61, valve 62, and holes in line 63 where cabinet air is heated by finned heater 64. The vapors drawn from line 50, through rotameter 56, valve 57, and line 58 into venturi aspirator 55, are mixed therein with the incoming heated air from line 75. The gaseous mixture created in aspirator 55 exhausts through line 80, which can lead to the basic sulfur recovery reactor from which the sample was originally obtained. Outside cabinet 10, line 80 is maintained at a sufficiently high temperature to keep sulfur in the liquid state. Vapors flowing through bypass line 50 are not subjected to analysis and the purpose of this bypass feature is to minimize transport time of the gaseous sample in the conditioner that is inside the cabinet. Typically, 80 to 90 percent of the vapors flowing through line 45 are sent through bypass line 80.

The portion of vapors flowing through line 45, that is eventually sent to analyzer chamber 200, is passed by a sample conveying line 54 through a normally open block valve 90 into line 95. The gaseous sample is then passed through a normally open valve 100 into line 110 which leads to analyzer 200. Line 110 is maintained at a desired temperature of about 300° to 400° F (149° – 204° C) until it enters analyzer 200 by means of hot air which flows from pipe 61 through heated conduit 115 surrounding line 110 (as well as all other lines interconnecting conditioning chamber 10 and analyzer 200), and connecting cabinet 10 with analyzer chamber 200. Hot air exits from conduit 115 through passageway 120. A plug 125, inserted at analyzer 200 end of the conduit 115, is a soft easily removable plug having three bores therethrough. Lines 110, 140, and 145, leading from cabinet 10 to analyzer chamber 200, fit closely inside the respective bores of plug 125 so that hot air flowing through conduit 115 surrounding lines 110, 140, and 145, is prevented from entering analyzer 200.

The vapors in sample line 110 flow into the analyzer section of the system and therein are permitted to enter a detection column (not shown) when sample valve 150 is operated. Any suitable gas analyzer, such as a gas chromatograph, can be employed in connection with this invention. During the analysis cycle period flow in line 145, 110, 167 and 155 is stopped by closing of solenoid valve 100. Three-way valve 152 is then actuated to place line 145 into communication with the atmosphere through line 180 so that the pressure in line 145 equalizes with the atmospheric pressure. The analyzed vapors are returned to the cabinet through return line 145, which leads from analyzer 200, through plug 125, and heated conduit 115, back to the cabinet 10. In the conduit the gases flowing through the return line 145 remain at the desired temperature as the result of air circulating from cabinet 10 through conduit 115 and exiting via passageway 120. Inside cabinet 10, the analyzed vapors flow in return line 145, past three-way valve 152, into line 155. From there, the vapors are directed through a rotameter 160, past flow control valve 165, into line 167, which discharges into line 58. The analyzed vapors are drawn into line 58 as the result of sub-atmospheric pressure maintained therein (as discussed earlier). The vapors flow into aspirator 55 and are discharged together with the bypass vapors and hot air through line 80. After the analyzed gas sample is exhausted from cabinet 10, normally closed valve 170 is opened and a portion of hot air from line 60 is allowed to pass through purge line 140. Purge line 140 connects with sample line 110 inside the analyzer and check valve 141 in line 140. The hot air flowing through the purge line 140 enters sample line 10 and flows through check valve 111 in line 110. The hot purge air passes through line 145, valve 152, line 155 through rotameter 160, valve 165, and line 167. From line 167, the purge air enters line 58 into aspirator 55 from which it is exhausted via 80. The hot air also flows through line 110 in the opposite direction from that of the sample gas and back through valve 100, line 95, valve 90, line 54, rotameter 56, line 58 to aspirator 55 from which it is exhausted through line 80. Purge air also flows through line 45 into liquid-vapor separator 25, sample line 12, past block valve 20 and exhausted through line 12 at the point at which the sample was originally introduced.

Purge air continues to flow, as described, until a predetermined time before another gas sample is to be taken. At this time, solenoid operated valve 170 closes and sample vapors again flow from the process sample point through line 12 as previously described.

For calibration, two-gas samples can be introduced into the analyzer. When calibration of the analyzer is started, sample vapor flow through line 54 is blocked by closing valve 90. Valve 182 is then opened and a calibrating gas is introduced from an external source via line 187 into line 95, and it is permitted to flow into the analyzer through line 110. Similarly, a different gas can be introduced from a second external source by closing valve 182, opening valve 182, and injecting the calibrating gas through 189. Two separate sources of calibrating gases are preferred when testing for hydrogen sulfide and sulfur dioxide, since it is not practical to store a mixture of these two gases in the same container for an extended period of time.

Air from heater 70 can be directed through line 60 to flow into line 12 by opening block valve 191 which is connected to line 45 through pipe 59 and liquid-vapor separator 25, if it is desired to do so for any reason such as for maintenance or repairs. In the drawing, certain of the valve handles are presented by dotted lines indicating that these handles preferably extend to the exterior of cabinet 10. If desired, all valve handles could be likewise extended.

The present invention overcomes a problem in the apparatus of U.S. Pat. No. 3,897,211, namely, the condensation of sulfur and other products in the line 110 carrying the sample gas between the conditioning cabinet and analyzer and related effects. Further in this connection, the air purged line 35 in U.S. Pat. No. 3,897,211 was connected inside the conditioning cabinet to the line 45 from the analyzer and, therefore, should any products condense within the line 45, the air purge line would carry the condensed products all into the analyzer, analyzer valve, etc. Since it is always important to keep condensation of products out of the sample valve in the analyzer which has very small passage ways, it is necessary to overcome this problem by better heating the lines in the conduit 115 going between the sample conditioner and analyzer. Further, the air purge line 140 now goes from the conditioning cabinet into the analyzer and connects in the analyzer housing 200 such that any condensation products will be purged out of the sample line via pipe 110 and not be allowed to enter the analyzer and analyzer valve 150. Further improvements are achieved by the use of check valves 111 and 141. The purpose of check valve 141 is to eliminate the effects of dead end line (such as 140 without valve 141) containing air which would diffuse into the sample and dilute the sample. The dead end line would contain air after a previous analysis which would dilute the sample. Further, a check valve 111 isolates the long section of line 110 which would have to be equalized in the pressure equalization step as when valve 152 is opened to the atmosphere. In the present invention when valve 152 is opened to the atmosphere, the pressure only equalizes to check valve 111 and not all the way back into the line 110 leading from the sample conditioner cabinet to the analyzer.

The present invention has been described with reference to a gaseous sample stream containing reactive hydrogen sulfide and sulfur dioxide. The conditioner of the invention can be similarly employed with advantage for conditioning gaseous samples when it is desired to maintain, for one reason or another, a sample to be analyzed at a high temperature and in applications where it is desired to prevent gaseous samples from remaining in the conditioner and analyzer for extended periods.

Various advantages of the conditioner of the invention are apparent from the foregoing. Thus, it will be apreciated that with use of the conditioner, condensation of gaseous materials can be avoided and the conditioner can operate for extended periods. Gaseous samples can be taken for analysis from remote points because of the bypass arrangement of the conditioner which provides rapid circulation of sample through the conditioner with a considerable driving force. The pressure of this gaseous sample is brought into equilibrium with atmospheric pressure within the analyzer before being introduced into the chromatographic analyzer column. A gaseous sample, which is both poisonous and/or noxious to humans, can be purged with air back into the process from which it came without escaping to the surrounding atmosphere.

Those modifications and equivalents which fall within the spirit of the invention are to be considered a part thereof.

I claim:

1. A device for the analysis of gases which contain reactive components comprising:
   a gas analyzer having a detection chamber;
   an enclosed heated conditioning cabinet having a heater within said cabinet to heat cabinet air;
   a heated conduit connecting said analyzer and said cabinet in open communication with said cabinet and heated by warmed cabinet air flowing from the cabinet through said conduit and having an opening near the analyzer end to exhaust warmed air from said cabinet and said conduit to the atmosphere;
   a plug at the analyzer end of said heated conduit adapted to prevent air flowing from said cabinet through said heated conduit and exiting through said opening from entering said analyzer;
   means for introducing a gas sample into said cabinet;
   bypass means for diverting a portion of said gaseous sample introduced into said cabinet and for exhausting it from said cabinet without analysis;
   sample conveying means for transporting a predetermined portion of said gaseous sample through said heated cabinet and said heated conduit and into said detection chamber, said sample conveying means including a sample line for carrying of said gaseous sample, extending from the cabinet through the conduit to the detection chamber of said analyzer;
   purging means for selectively purging said sample conveying means with air, said purging means including a purge line for carrying of air, leading from the cabinet through said heated conduit and said plug and into said analyzer, said purge line being in open communication with said sample line; and
   means for withdrawing a portion of said gaseous sample from said detection chamber of the analyzer to the cabinet and for exhausting it from said cabinet, said sample withdrawing means including a line leading from the analyzer through said heated conduit into said cabinet.

2. Apparatus as set forth in claim 1 having a Venturi section associated with said bypass means within said cabinet which serves as a driving force for directing and exhausting a portion of said gaseous sample from said cabinet and for conveying another portion of said sample to analyzing means.

3. Apparatus as set forth in claim 1 having separate means for introducing a calibrating gas into said cabinet and to said sample conveying means.

4. Apparatus as set forth in claim 1 having a heater within said cabinet for heating the purging air.

5. Apparatus as set forth in claim 1 having two separate means for introducing two calibrating gases into said cabinet and to said sample conveying means.

6. Apparatus as set forth in claim 1 having means within said heated cabinet for separating liquids present in said gaseous sample.

* * * * *